US012702388B2

(12) United States Patent
Ralph et al.

(10) Patent No.: US 12,702,388 B2
(45) Date of Patent: Aug. 11, 2026

(54) NEEDLE WITH CONTIGUOUS INTERRUPTED AND UNINTERRUPTED HELICAL-CUT SECTIONS

(71) Applicant: GYRUS ACMI, INC., Westborough, MA (US)

(72) Inventors: Christopher Ralph, Woodinville, WA (US); Jason T. Panzenbeck, Redmond, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 605 days.

(21) Appl. No.: 17/936,288

(22) Filed: Sep. 28, 2022

(65) Prior Publication Data

US 2023/0108441 A1 Apr. 6, 2023

Related U.S. Application Data

(60) Provisional application No. 63/251,299, filed on Oct. 1, 2021.

(51) Int. Cl.
*A61B 10/02* (2006.01)
*A61B 17/00* (2006.01)

(52) U.S. Cl.
CPC .................... *A61B 10/0233* (2013.01); *A61B 2017/00309* (2013.01)

(58) Field of Classification Search
CPC ................ A61B 10/0233; A61B 10/04; A61B 2010/045; A61B 2017/00309; A61M 25/0138; A61M 25/0054
See application file for complete search history.

(56) References Cited

U.S. PATENT DOCUMENTS

2013/0225997 A1* 8/2013 Dillard ............... A61B 10/0283 29/896.9
2014/0276051 A1 9/2014 Hoffman
(Continued)

FOREIGN PATENT DOCUMENTS

CN 112638240 A 4/2021
CN 115886886 4/2023
(Continued)

OTHER PUBLICATIONS

"Japanese Application Serial No. 2022-158617, Response filed Jan. 4, 2024 to Notification of Reasons for Rejection mailed Oct. 2, 2023", w english claims, 11 pgs.
(Continued)

*Primary Examiner* — Devin B Henson
(74) *Attorney, Agent, or Firm* — Schwegman Lundberg & Woessner, P.A.

(57) ABSTRACT

Disclosed embodiments include apparatuses, systems, and methods for sampling a targeted region of tissue in a body using a flexible needle including a plurality of interrupted cuts and an uninterrupted cut extending continuously from the uninterrupted cuts to reduce localized strain on the flexible needle. In an illustrative embodiment, an apparatus includes a flexible needle, where the flexible needle includes: a proximal end; a distal end including a needle tip; and a shaft extending between the proximal end and the distal end and including a flexible portion, where the flexible portion includes; an interrupted cut section including a plurality of interrupted cuts in the shaft following a first helical pattern; and an uninterrupted cut section including an uninterrupted cut in the shaft following a second helical pattern where the uninterrupted cut extends continuously from an end of a first terminal cut at a first end of the interrupted cut section.

21 Claims, 10 Drawing Sheets

(56) References Cited

U.S. PATENT DOCUMENTS

| | | | | |
|---|---|---|---|---|
| 2015/0342580 | A1* | 12/2015 | Clancy ............... | A61B 17/3417 600/567 |
| 2019/0275260 | A1 | 9/2019 | Ralph et al. | |
| 2020/0078047 | A1* | 3/2020 | Lambe ................. | A61B 1/2676 |
| 2021/0213243 | A1 | 7/2021 | Guo et al. | |

FOREIGN PATENT DOCUMENTS

| | | |
|---|---|---|
| DE | 102022124478 | 4/2023 |
| EP | 3566739 | 11/2019 |
| JP | 2016505299 | 2/2016 |
| JP | 2017533012 | 10/2018 |
| JP | 2021520858 | 8/2021 |
| WO | 2014164237 | 10/2014 |

OTHER PUBLICATIONS

"Japanese Application Serial No. 2022-158617, Examiners Decision of Final Refusal mailed Mar. 11, 2024", w English translation, 5 pgs.

"Japanese Application Serial No. 2022-158617, Notification of Reasons for Rejection mailed Oct. 2, 2023", W English Translation, 7 pgs.

"Chinese Application Serial No. 202211217559.0, Office Action mailed Jan. 23, 2025", w/ English translation, 20 pgs.

"Chinese Application Serial No. 202211217559.0, Response filed May 9, 2025 to Office Action mailed Jan. 23, 2025", w/ english claims, 13 pgs.

"Japanese Application Serial No. 2022-158617, Appeal of an Adverse Decision—Overseas Applicant filed Jul. 11, 2024", W/English Claims, 19 pgs.

"Japanese Application Serial No. 2022-158617, Notification of Reasons for Refusal mailed May 20, 2025", w/ English translation, 4 pgs.

"Chinese Application Serial No. 202211217559.0, Response filed Sep. 30, 2025 to Office Action mailed Aug. 5, 2025", w/ English Claims, 44 pgs.

"Chinese Application Serial No. 202211217559.0, Office Action mailed Aug. 5, 2025", W English Translation, 12 pgs.

"Japanese Application Serial No. 2022-158617, Response filed Aug. 20, 2025 to Notification of Reasons for Refusal mailed May 20, 2025", w English Claims, 10 pgs.

* cited by examiner 100
110
112
150
142
140
120
130
132
116
118
114

201
132
α
232
130
120
260
140
262
β
242
142

900
905
910

1000
1010

1100
1105
1110

1200

1300

1400

| PART NO. | A | B | C | D |
|---|---|---|---|---|
| E1493-01 | 115 / 29 | 2.5 | .005 | 500 |
| E1493-02 | 85 / 59 | 2.5 | .005 | 500 |
| E1493-03 | 30 / 50 | 4.5 | .005 | 900 |
| E1493-04 | 60 / 20 | 4.5 | .005 | 900 |
| E1493-05 | 30.5 / 35 | 5.5 | .005 | 1100 |
| E1493-06 | 45 / 20.5 | 5.5 | .005 | 1100 |
| E1493-07 | 115 / 29 | 2.5 | .008 | 313 |

NEEDLE WITH CONTIGUOUS INTERRUPTED AND UNINTERRUPTED HELICAL-CUT SECTIONS

FIELD

Disclosed embodiments relate to flexible needles and their formation.

BACKGROUND

The statements in this section merely provide background information related to the present disclosure and may not constitute prior art.

Long, flexible needles may be highly useful for retrieving samples of tissue within a body. Such needles may be inserted through catheters or other lumens to reach structures inside a body to collect a tissue sample from a targeted region of tissue, thereby potentially avoiding use of a more invasive procedure to get the sample.

Although such needles should have a certain degree of flexibility to enable the needle to follow a potentially tortuous path to reach the targeted region, for example, by bending to conform a curved or angled path, such needles also require sufficient column strength to enable the needle to be pushed into position and/or inserted into the targeted region. One way to make such needles flexible is to form cuts in the walls of the needle. However, such cuts may make the needle too flexible or may result in localized stresses at ends of the cuts.

SUMMARY

Disclosed embodiments include apparatuses, systems, and methods relating to a flexible needle that includes a plurality of interrupted cuts and an uninterrupted cut extending continuously from the uninterrupted cuts to reduce localized strain on the flexible needle.

In an illustrative, non-limiting embodiment, an apparatus includes a flexible needle, where the flexible needle includes: a proximal end; a distal end including a needle tip; and a shaft extending between the proximal end and the distal end and including a flexible portion, where the flexible portion includes; an interrupted cut section including a plurality of interrupted cuts in the shaft following a first helical pattern; and an uninterrupted cut section including an uninterrupted cut in the shaft following a second helical pattern where the uninterrupted cut extends continuously from an end of a first terminal cut at a first end of the interrupted cut section.

In another illustrative, non-limiting embodiment, a system for sampling a targeted region of tissue includes: an insertion system configured to receive an elongated instrument into a proximal end of a lumen and to convey a distal end of the lumen into a body toward a targeted region of tissue to be sampled; and a flexible needle assembly configured to be insertable into the body via the lumen, where the flexible needle assembly includes: a flexible needle, where the flexible needle includes: a proximal end; a distal end including a needle tip; and a shaft extending between the proximal end and the distal end and including a flexible portion, where the flexible portion includes: an interrupted cut section including a plurality of interrupted cuts in the shaft following a first helical pattern; and an uninterrupted cut section including an uninterrupted cut in the shaft following a second helical pattern where the uninterrupted cut extends continuously from an end of a first terminal cut at a first end of the interrupted cut section; and a handle assembly configured to engage the proximal end of the flexible needle and to control movement of the flexible needle.

In another illustrative, non-limiting embodiment, a method includes producing a needle shaft having a proximal end and a distal end including a needle tip; forming a plurality of interrupted cuts through a wall of the shaft where the plurality of interrupted cuts follow a first helical pattern; and forming an uninterrupted cut in the shaft through the wall of the shaft, where the uninterrupted cut extends continuously from an end of a first terminal cut at a first end of the plurality of interrupted cuts and the uninterrupted cut follows a second helical pattern.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings.

DETAILED DESCRIPTION

Figures 1, 2:
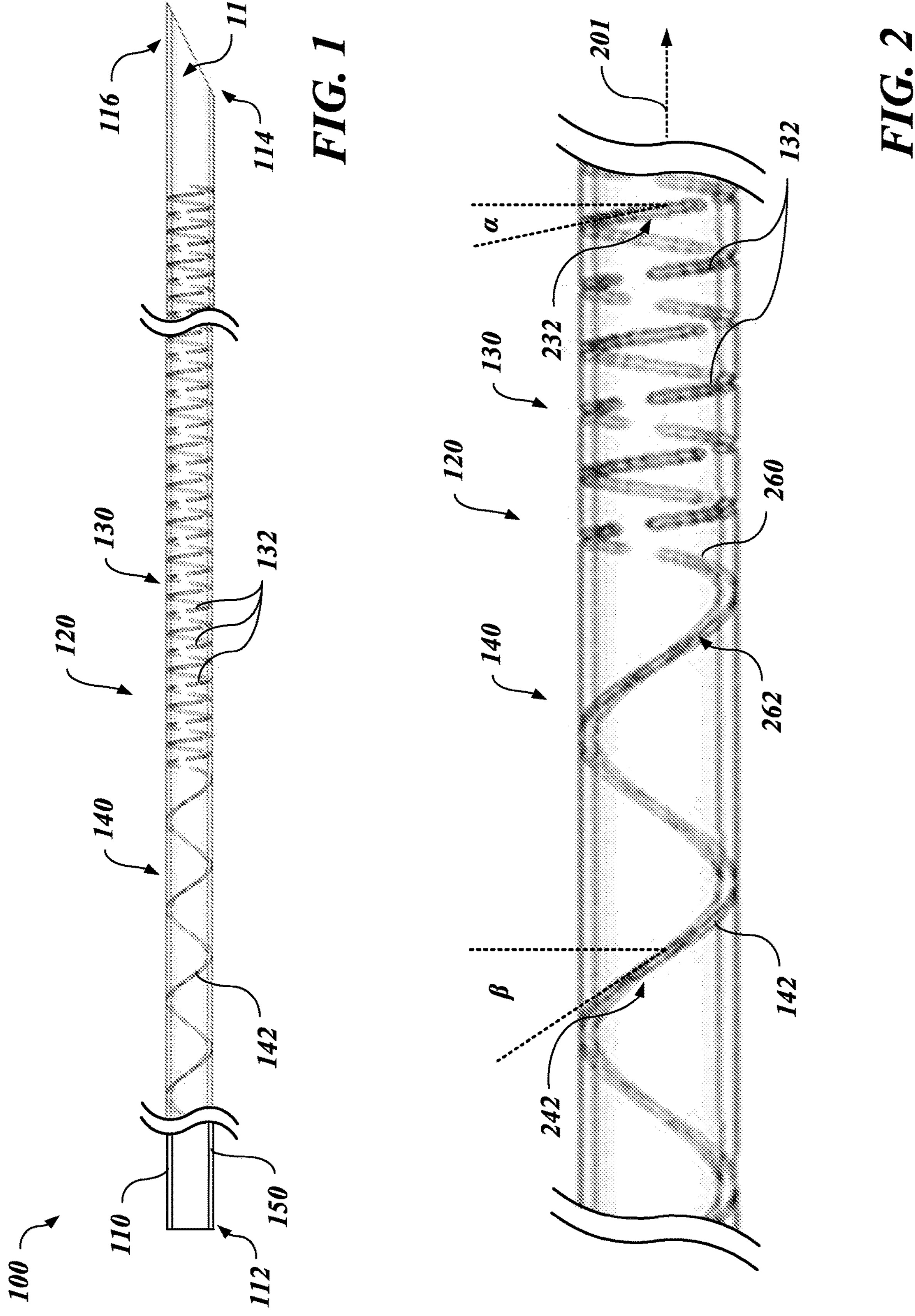
FIGS. 1-8 are side plan views in partial cutaway form of a flexible needle having interrupted cuts extending continuously into an uninterrupted cut.

The following description is merely illustrative in nature and is not intended to limit the present disclosure, application, or uses. The terminology used in the description presented herein is not intended to be interpreted in any limited or restricted manner. Rather, the terminology is simply used in conjunction with a detailed description of embodiments of the apparatuses, systems, methods and related components. Furthermore, embodiments may comprise several novel features, no single one of which is solely responsible for its desirable attributes or is believed to be essential to practicing the disclosed embodiments herein described.

By way of a non-limiting introduction and overview, in various embodiments, an apparatus includes a flexible needle. The flexible needle includes a shaft extending from a proximal end to a distal end from which a needle tip extends. The shaft includes a flexible portion that includes an interrupted cut section and an uninterrupted cut section. The interrupted cut section includes a series of interrupted cuts in the shaft, where the individual cuts that make up the series follow a first helical pattern. The first helical pattern may have a constant pitch or a variable pitch. The uninterrupted cut section includes an uninterrupted cut in the shaft following a second helical pattern. The uninterrupted cut extends continuously from an end of a first terminal cut at a first end of the interrupted cut section. The uninterrupted cut section, extending continuously from the end of the interrupted cut section, redistributes stress placed on the first end of the uninterrupted cut section, helping to prevent deformation, bending, or breaking of the shaft of the needle along the flexible portion. In this regard, although interrupted cuts provide for adequate flexibility and column strength for extending a needle from a catheter following a tortuous path, many existing needles exclusively utilize uninterrupted cut patterns due to the stress concentrations resulting at transitions between an interrupted cut and an uncut needle section. It is an object of the presently disclosed needle configurations to obtain the benefits of superior column strength provided by interrupted cuts while mitigating the formation of such stress concentrations at a terminal end thereof by positioning an uninterrupted cut contiguous with the terminal end of the interrupted cut.

It will be appreciated that the use of uninterrupted cuts has been thought to be preferable to using interrupted cuts because of the possibility of localized stress or strain caused by uninterrupted cuts. For example, U.S. Patent Application Publication No. US2013/0225997A1 stated that, "continuous patterns are desired over interrupted patterns because of improved resistance to fatigue failures and improved flexure characteristics." See, e.g., U.S. Patent Application Publication No. US2013/0225997A1, Paragraph 0084. In various embodiments, an uninterrupted cut extending continuously from a series of uninterrupted cuts may disperse localized stress and strain and thereby alleviate fatigue or similar concerns.

The flexible needle may be joined with a handle and used with an insertion system to secure samples of tissue from a targeted region in a body.

Now that a general overview has been given, details of various embodiments will be explained by way of non-limiting examples given by way of illustration only and not of limitation.

Referring to FIG. 1, a flexible needle 100 includes a shaft 110 that extends from a proximal end 112 to a distal end 114. In various embodiments, a needle tip 116 extends from the distal end 114 and forms an opening 118 that may be used, for example, to extract or retrieve a tissue sample, as further described below, or to inject a substance at a selected location.

In various embodiments, the shaft 110 includes a flexible portion 120. The flexible portion 120 includes an interrupted cut section 130 that includes multiple interrupted cuts 132. The flexible portion 120 also includes an uninterrupted cut section 140 that includes a single, uninterrupted cut 142. In various embodiments, both the interrupted cuts 132 and the interrupted cut 142 may be formed by a laser that cuts through a wall 150 of the shaft 110.

Referring additionally to FIG. 2, considering an enlarged view of the flexible portion 120, it will be appreciated that each of the multiple interrupted cuts 132 and the single, uninterrupted cut 142 follow helical patterns 232 and 242, respectively. In various embodiments, the first helical pattern 232 of the interrupted cuts 132 is disposed at a first pitch angle α relative to an axis 201 of the shaft 110 and the second helical pattern 242 of the uninterrupted cut 142 is disposed at a second pitch angle β relative to the axis 201 of the shaft 110. It will be appreciated that a smaller pitch angle, by providing more openings to enable more flexing per unit length of the shaft 110, generally provides greater flexibility than a larger pitch angle. It will also be appreciated that the interrupted cuts 132 provide less flexibility than uninterrupted cuts of a same pitch angle because the interruptions in the interrupted cuts 132 are more resistant to flexing than the cuts themselves. A benefit of interrupted cuts over uninterrupted cuts is a greater degree of column strength and, therefore, in many applications such as when a needle is to be forced out of a sampling device via a needle ramp interrupted cuts provide an appropriate degree of both flexibility and column strength. However, it has been observed in previous needle designs that transitioning an interrupted helical cut section directly to an uncut needle section results in a stress concentration which can lead to needle breakage (e.g., mechanical failure at the point of transition).

As used herein, the term "interrupted cut" refers to a cut pattern which includes a plurality of through cuts (e.g., which may be formed via laser cutting techniques) which traverse radially around a needle a number of degrees before being interrupted by an uncut section of a number of degrees. In various embodiments, for example, an interrupted cut may include a cut pattern having a first cut which traverses radially around a needle, along a helical path, for 115 degrees (e.g., about 2 radians) before being interrupted by a first uncut section of 29 degrees (e.g., about 0.5 radians) after which a second cut begins along the same helical path and traverses for another 115 degrees before being interrupted by a second uncut section of 29 degrees, and so on.

In various embodiments, the uninterrupted cut 142 extends continuously from an end 262 of a first terminal cut 260 at an end of the interrupted cuts 132. As noted above, without the uninterrupted cut 142 extending continuously from the end 262 of the first terminal cut 260, stress and strain applied along the uninterrupted cut section 130 may become localized at the end 262 of the first terminal cut 260. The localization of the stress and strain could result in undesired deformation of the shaft 110, resulting in bending, cracking, and/or breaking of the shaft. 110. In various embodiments of the flexible needle 100, the stress and strain exerted at the first terminal cut 260 is received and dispersed by the continuous cut 142. The presence of the uninterrupted cut 142 adjacent to the end 262 of the first terminal cut 260 at the end of the interrupted cuts 132 significantly lessens the degree of this undesirable stress localization and, therefore, prevents the needle breakage observed in previous needle designs.

In an embodiment as shown in FIG. 2, where the second pitch angle β of the uninterrupted cut section 140 is greater than the first pitch angle α of the interrupted cut section 130, the uninterrupted cut section 140 may be less flexible than the interrupted cut section 130, as previously described. However, the uninterrupted cut section 140 nonetheless will be more flexible than an uncut section of the shaft 110. As a result, the uninterrupted cut section 140 provides more rigidity to the shaft 110, but provides more flexibility than an uncut section to disperse stress and strain applied at the end 262 of the interrupted cut section 130 of the shaft 110.

In the embodiment of FIG. 1, the interrupted cut section 130 is disposed along the shaft 110 between the distal end 114 and the uninterrupted cut section 140. In this configuration, with the interrupted cut section 130 having a lower, first pitch angle α than the second pitch angle β of the uninterrupted cut section 140, the flexible needle 100 will be more flexible toward the distal end 114 of the shaft 110 than it is along the uninterrupted cut section 140. However, in other embodiments, it may be desirable for the shaft 110 to be more rigid toward the distal end 114 of the shaft.

Figures 3, 4, 5:
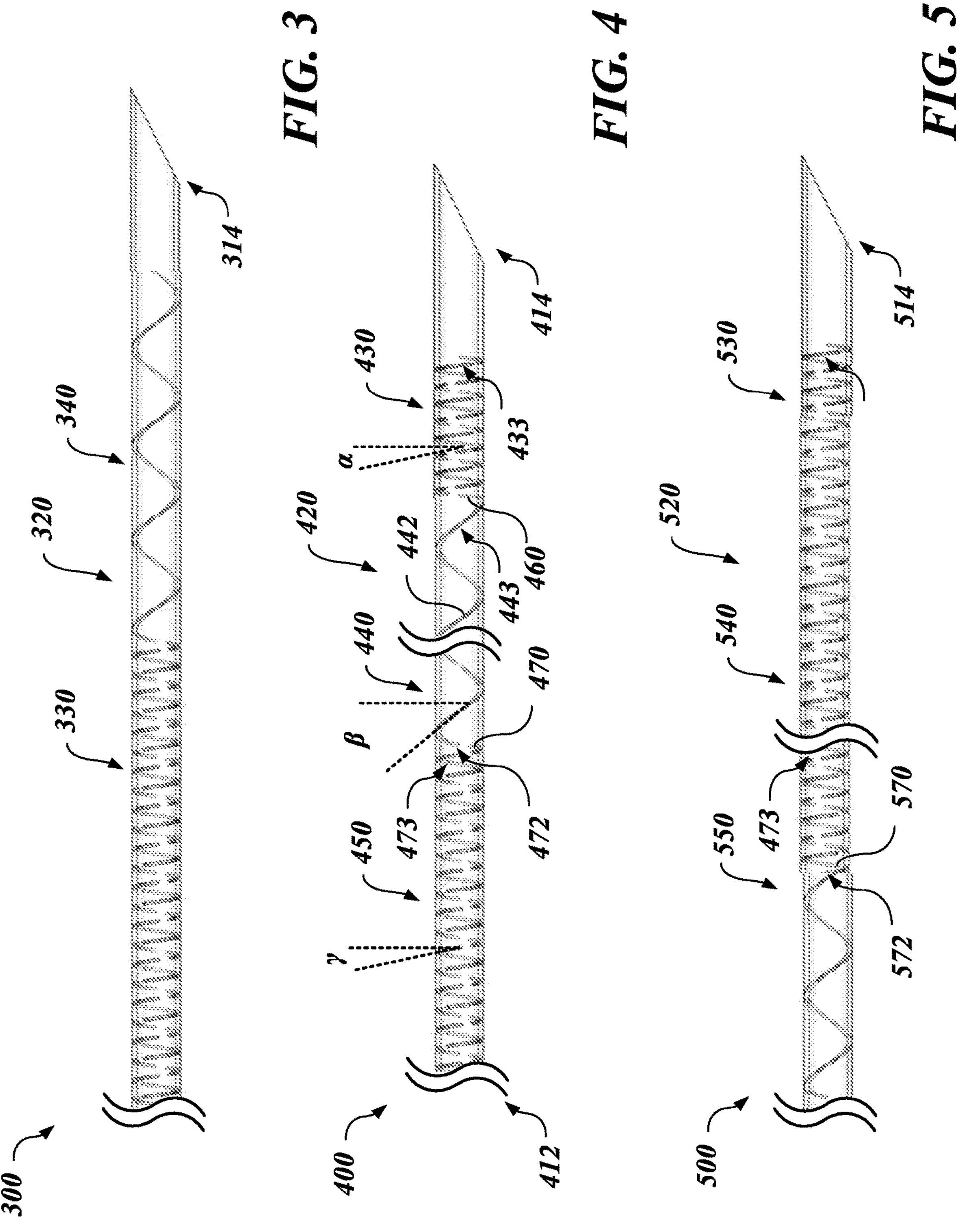

Referring additionally to FIG. 3, in various embodiments, a flexible needle 300 includes a flexible portion 320 with an uninterrupted cut section 340 positioned between a distal end 314 of the flexible needle 300 and an interrupted cut section 330. In such an embodiment, with the cut sections 330 and 340 having the same pitch angles as the cut sections 130 and 140 as the flexible needle 100 of FIGS. 1 and 2, the uninterrupted cut section 340 being positioned closer to the distal end 314 will make the flexible needle 300 more rigid toward the distal end 314.

In various embodiments, it may be desirable to include more than two cut sections to form a flexible needle that has varied flexibilities along its length. Referring additionally to FIG. 4, a flexible needle 400 includes a flexible portion 420 that includes three cut sections 430, 440, and 450. An uninterrupted cut section 440 extends continuously from an interrupted cut section 430 adjacent a distal end 414 of the flexible needle 400, as in the embodiment of FIG. 1. However, the flexible needle 400 also includes a second interrupted cut section 450 that continuously extends from an opposing end 472 of an uninterrupted cut 462 from an end 463 extending from a first terminal cut 460 of the first interrupted cut section 430. The second interrupted cut section 450 may include a third helical pattern 473 having a third pitch angle γ. The third helical pattern 473 may be the same or different than a first helical pattern 433 of a first interrupted cut section 430 having a first pitch angle α and/or a second helical pattern 443 of an uninterrupted cut section 440 having a second pitch angle β. The additional interrupted cut section may provide some desired flexibility in the flexible needle 400 rearward of the uninterrupted cut section 440. The pitch angles α, β, and γ may be changed to make each of the sections 430, 440, and 450 to provide a desired degree of flexibility in each of the sections 430, 440, and 450.

As described with reference to FIG. 4, in various embodiments, it may be desirable to include an uninterrupted cut section 440 between two interrupted cut sections 420 and 440. In various other embodiments, it also may be desirable to include an interrupted cut section between two uninterrupted cut sections. Such an embodiment may allow for a flexible but relatively stiff portion of a flexible needle near a distal end of the flexible needle while providing a more flexible portion adjacent to this section while including another uninterrupted portion to disperse stresses on the interrupted cut section.

Referring additionally to FIG. 5, a flexible needle 500 includes a flexible portion 520 that includes three cut sections 530, 540, and 550. An interrupted cut section 540 extends continuously from an uninterrupted cut section 530 adjacent a distal end 514 of the flexible needle 500. The flexible needle 500 also includes a second interrupted cut section 550 that continuously extends from an opposing end 572 of a second terminal cut 570 of the interrupted cut section 540. As described with reference to FIG. 4, pitch angles of helical patterns of each of the cut sections 530, 540, and 550 may be configured and/or varied to impart each of the cut sections 530, 540, and 550 with a desired degree of flexibility and/or relative flexibility as compared to the flexibility of the other sections, as further described below.

Figure 6A:
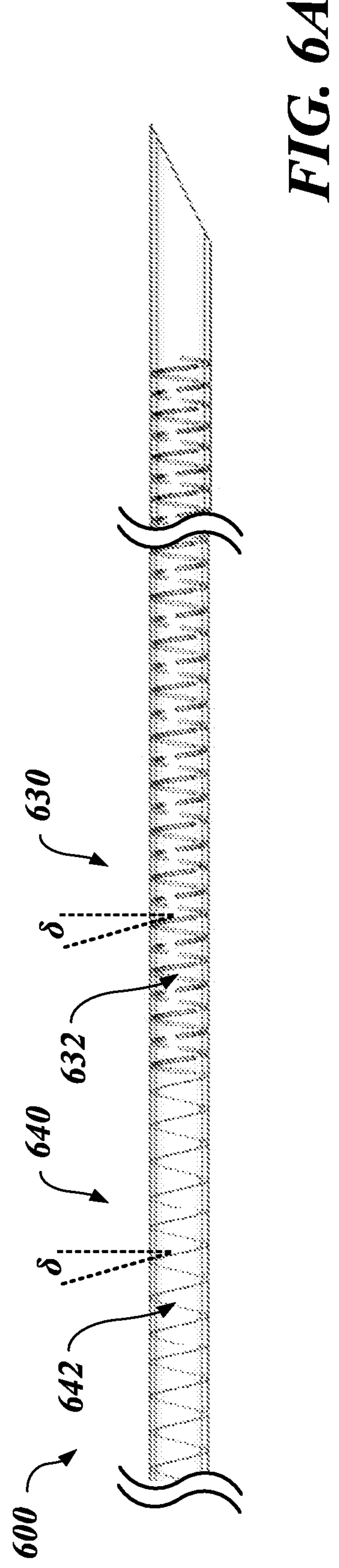

Referring additionally to FIGS. 6A, 6B, 7, and 8, the pitch angles of the helical patterns of the cut sections may be varied to provide desired degrees of flexibility of each of the cut sections. Referring additionally to FIG. 6A, a flexible needle 600 includes one interrupted cut section 630 and one uninterrupted cut section 640 extending continuously therefrom as previously described with reference to FIGS. 1 and 2. In the example of FIGS. 1 and 2, the uninterrupted cut section 130 and the interrupted cut section 140 had helical patterns 232 and 242 having different pitch angles α and β, respectively. In the example of FIG. 6A, the cut sections 630 and 640 have the same helical patterns 632 and 642 having a same pitch angle δ. It will be appreciated that the interrupted cut section 630, although having the same pitch angle δ as the uninterrupted cut section 640, will be less flexible because of the uninterrupted cuts. In any case, the pitch angles of the various cut sections may be different or the same to provide degrees of flexibility to suit different applications.

Figure 6B:
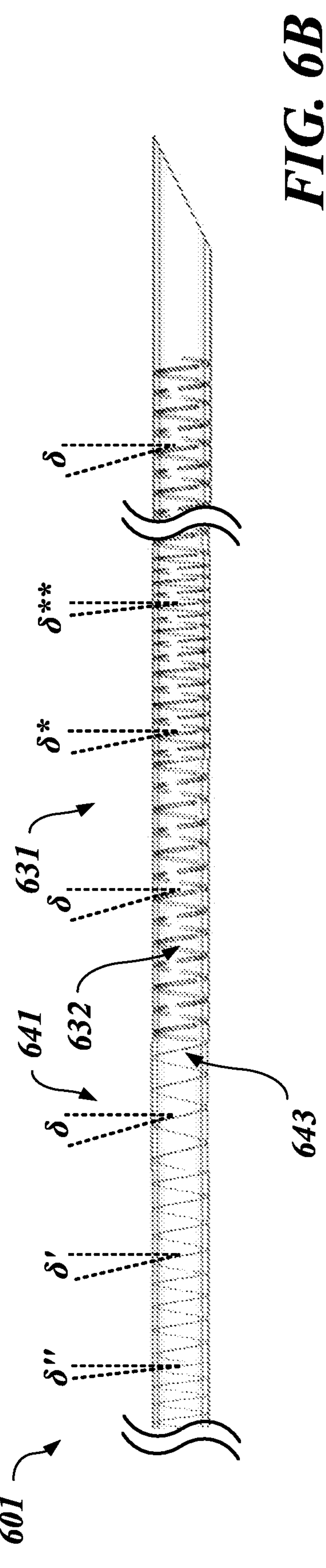

Referring additionally to FIG. 6B, it will be appreciated that the pitch angle may be variable as well as or instead of fixed in one or more of the cut sections. A flexible needle 601 includes an interrupted cut section 631 in which the pitch angle is varied, for example, from δ to δ* to δ** back to δ. In an uninterrupted cut section, the pitch angle is varied from δ to δ' to δ". There are no restrictions on the size of the pitch angle, and the pitch angle may be varied and/or variable throughout any of the interrupted cut sections or interrupted cut sections.

Figure 7:
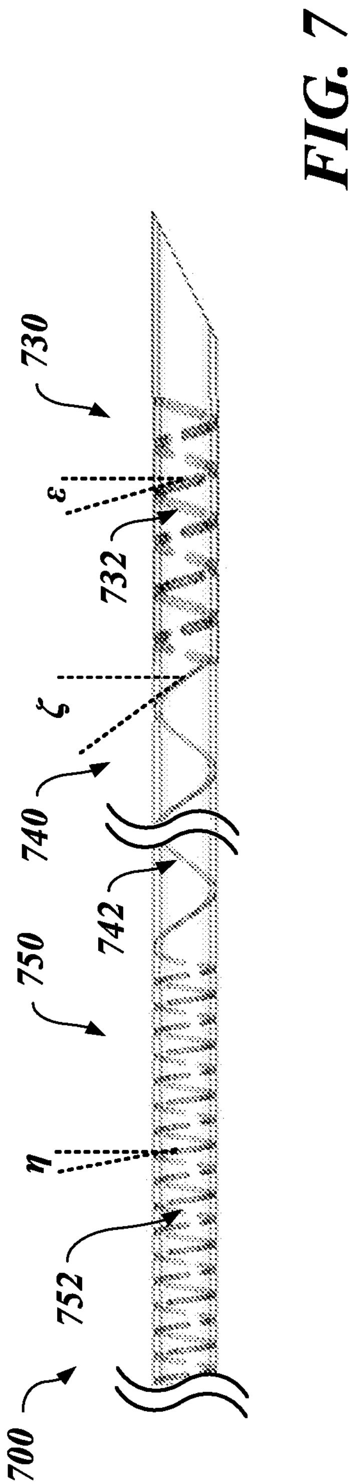
Figure 8:
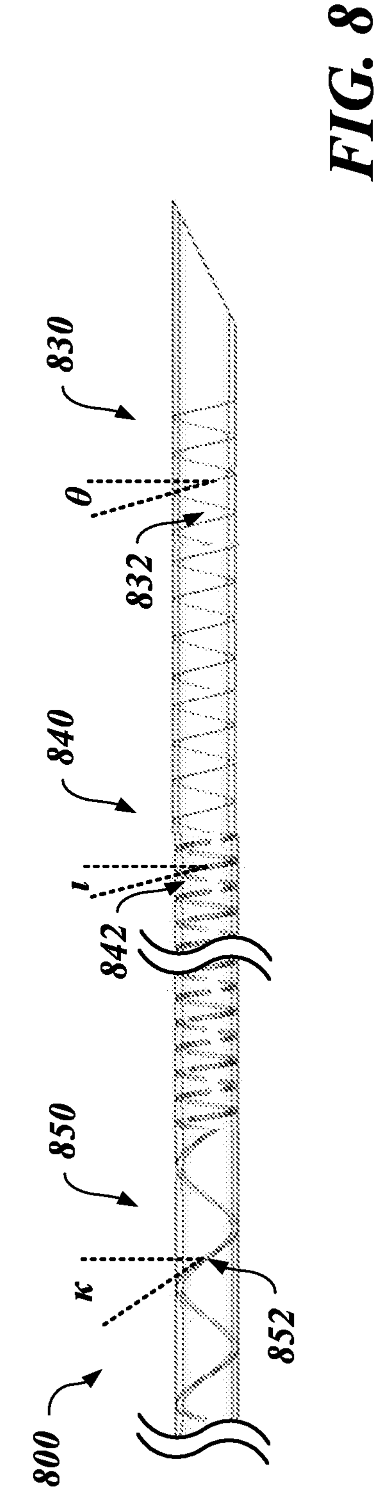

The pitch angles also may be the same or varied as desired with more than two cut sections, as described with reference to FIGS. 7 and 8. Referring additionally to FIG. 7, a flexible needle 700 has three cut sections 730, 740, and 750, including a first interrupted cut section 730 having a first helical pattern 732, a first uninterrupted cut section 740 having a second helical pattern 742, and a second interrupted cut section 750 having a third helical pattern 752. Each of the helical patterns 732, 742, and 752 may have different or equal pitch angles ¿, ¿, and n, respectively. Referring additionally to FIG. 8, a flexible needle 800 has three cut sections 830, 840, and 850, including a first uninterrupted cut section 830 having a first helical pattern 832, a first interrupted cut section 840 having a second helical pattern 842, and a second uninterrupted cut section 850 having a third helical pattern 852. Each of the helical patterns 832, 842, and 852 may have different or equal pitch angles θ, ι, and κ, respectively. Various embodiments are not limited as to the number of cut sections, the relative positioning of interrupted and uninterrupted cut sections, or the pitch angles of the helical patterns followed by the cuts. These configurations may be varied to provide different degrees of flexibility along a shaft of a flexible needle to suit any desired application.

Figures 9, 10, 11:
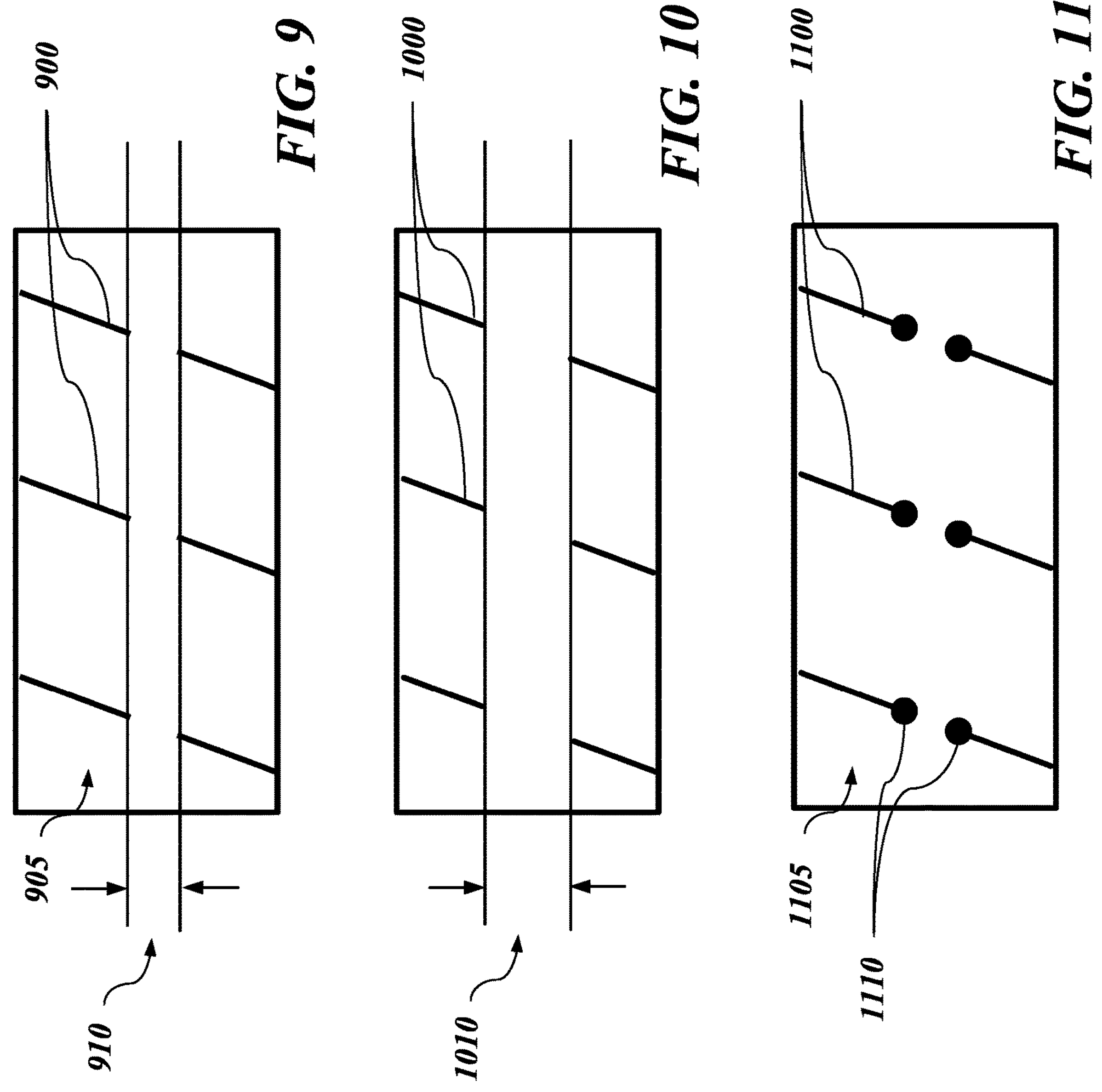
FIGS. 9-14 are side plan views of various forms of interrupted cuts.

Referring additionally to FIGS. 9-14, the cuts may be in various forms. Different cut shapes, like different pitch angles, may affect the relative flexibility or column strength of a cut section. Referring additionally to FIG. 9, uninterrupted cuts (not shown) and interrupted cuts 900 may be linear across the surface of the shaft 905. It will be appreciated that a gap 910 between the interrupted cuts 900 may be aligned. Offsetting the gap 910 may undermine the flexibility imparted by the interrupted cuts 900 because the solid portions of the shaft 905 may resist flexing of the shaft 905. Comparing FIGS. 9 and 10, in various embodiments, the gaps 910 and 1010 between interrupted cuts 900 and 1000 may be varied in size. It will be appreciated that, the smaller the size of the gaps 910 and 1010, the more flexible the shaft 905 will be.

Referring additionally to FIG. 11, the cuts 1100, whether linear in shape or not, may have rounded ends 1110. The rounded ends 1110 serve to disperse stress and strain across a surface of the shaft 1105 at the ends of the cuts 1100. Size of the rounded ends may vary to achieve a desired degree of dispersal of strain or stress across a surface of the shaft 1105.

The holes may cut in the surface of the shaft 1105 by lasers, just as the cuts themselves may be formed, as previously described.

Figures 12, 13, 14:
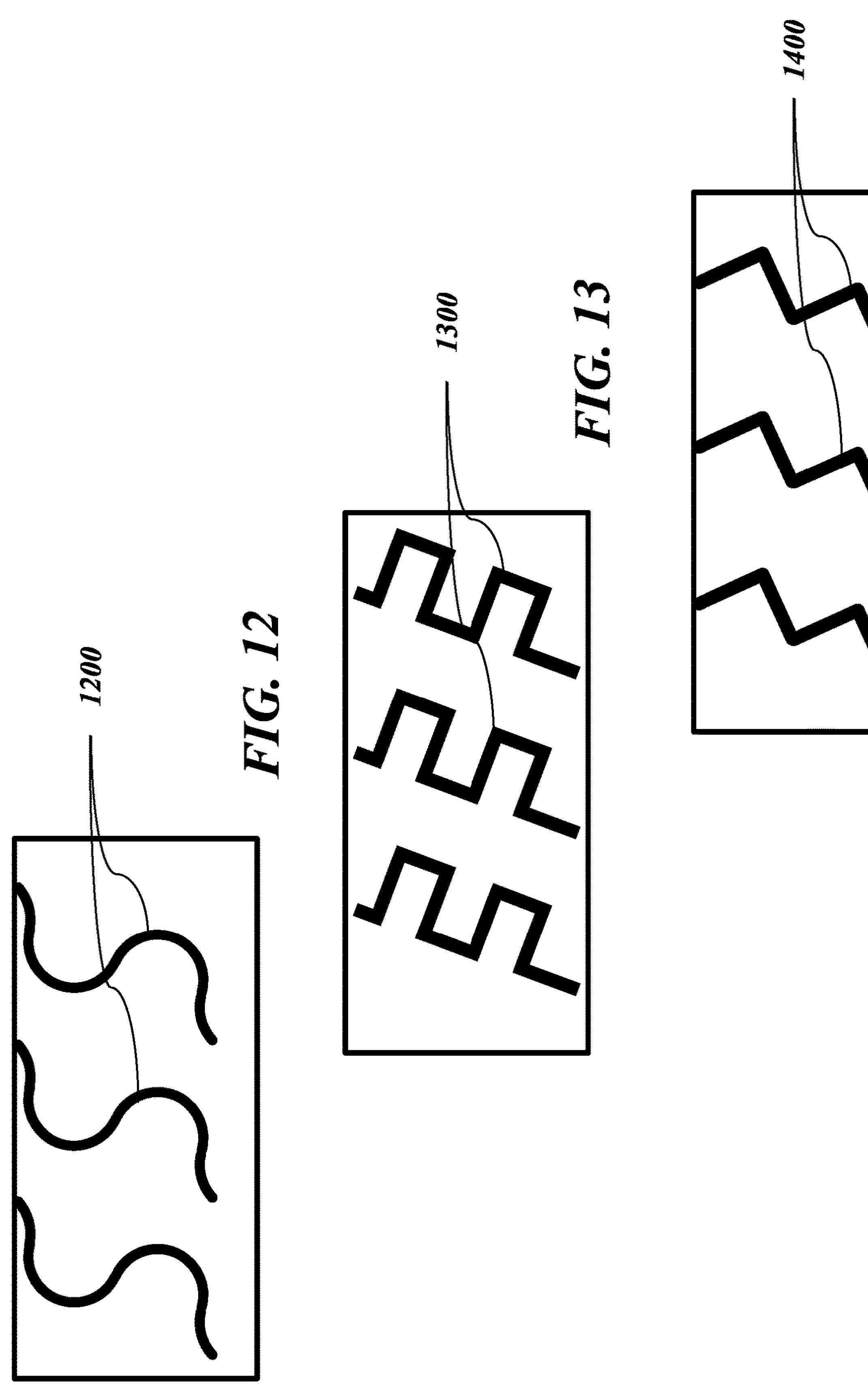

In addition to or instead of linear cuts, as described with reference to FIGS. 9-11, the interrupted cuts also may be made in forms other than linear cuts. Referring additionally to FIGS. 12-14, in various embodiments, sinusoidal cuts 1200 (FIG. 12), jigsaw-shaped cuts 1300 (FIG. 13), and zigzag-shaped cuts 1400 (FIG. 14) may be used. Such nonlinear cuts may serve to distribute stress and strain across the surfaces of the shaft more than linear cuts and/or may reduce the flexibility added as compared to linear cuts.

Figure 15:
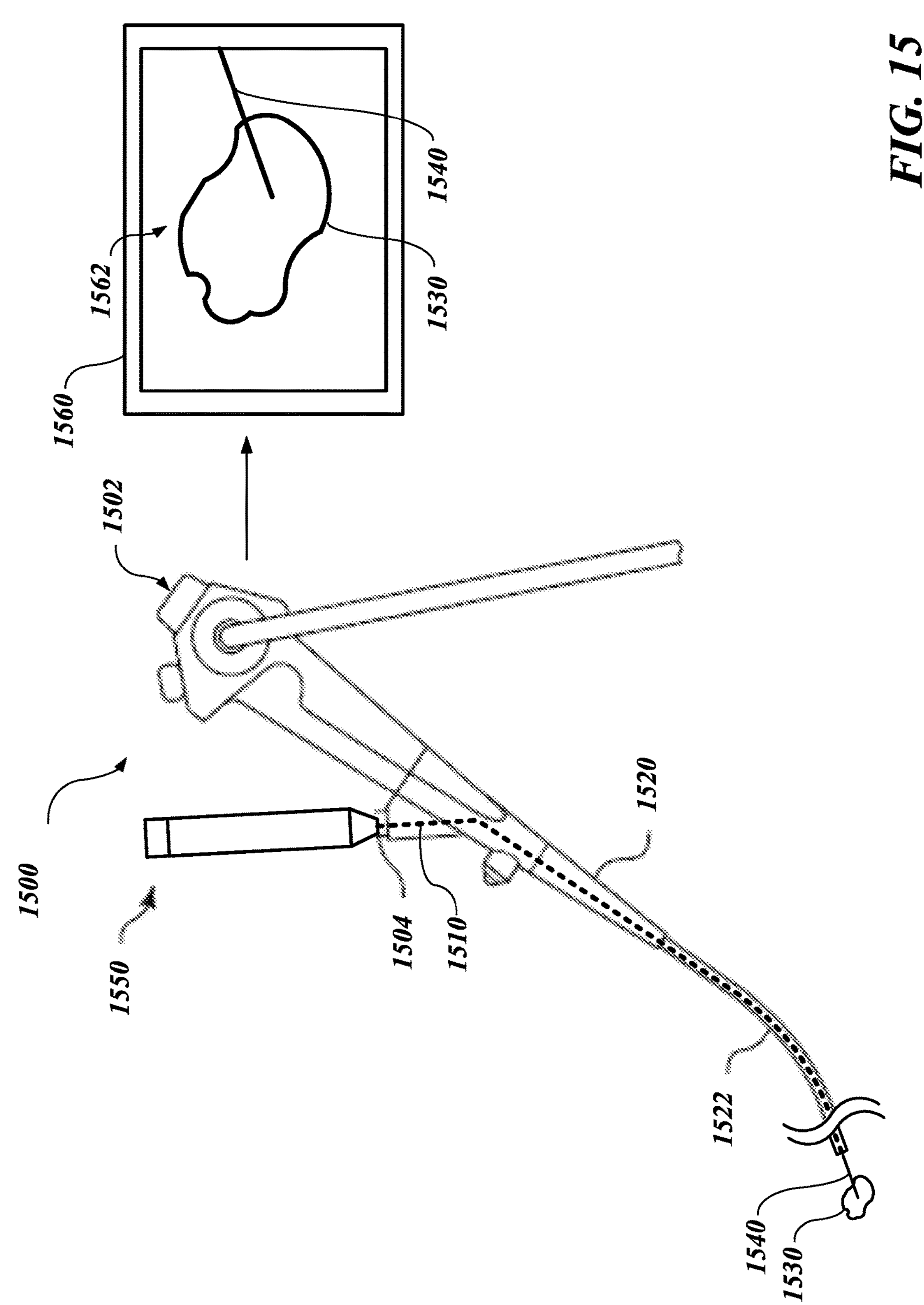
FIG. 15 is a side plan view of an insertion system including a flexible needle assembly.

Embodiments of the flexible needle may be used with an insertion system to obtain a sample of a targeted region of a tissue within a body. Referring additionally to FIG. 15, an insertion system 1500 includes a control interface 1502 that includes a port 1504 configured to receive an elongated instrument, such as the flexible needle 1510 (shown in dotted lines as inserted via the insertion system 1500). The control interface 1502 controls an insertion mechanism 1520 that directs and insertion tube 1522 to mechanically and/or electrically steers the insertion tube 1522 to a targeted region of tissue 1530 so that it can be sampled by a distal end 1540 of the flexible needle 1510. In various embodiments, the flexible needle 1510 is coupled with a handle 1550 that may be used to manipulate the flexible needle 1510. For example the handle 1550 may be used to facilitate insertion of the flexible needle 1510 within the insertion device 1500 and/or to manipulate the flexible needle 1510 in order to take a sample of the targeted region of tissue 1530.

In various embodiments, the insertion system 1500 may include an imaging system, as further described below. The imaging system may operate with a display 1560 to show imaging data 1562 of the targeted region of tissue 1530 and/or the distal end 1540 of the flexible needle 1510 to aid an operator in manipulating the insertion device 1500 and the flexible needle 1510 to obtain a sample. In various embodiments, the imaging data 1562 includes ultrasound imaging data, visual data, or other imaging data usable to envision the sample collection process.

Figure 16:
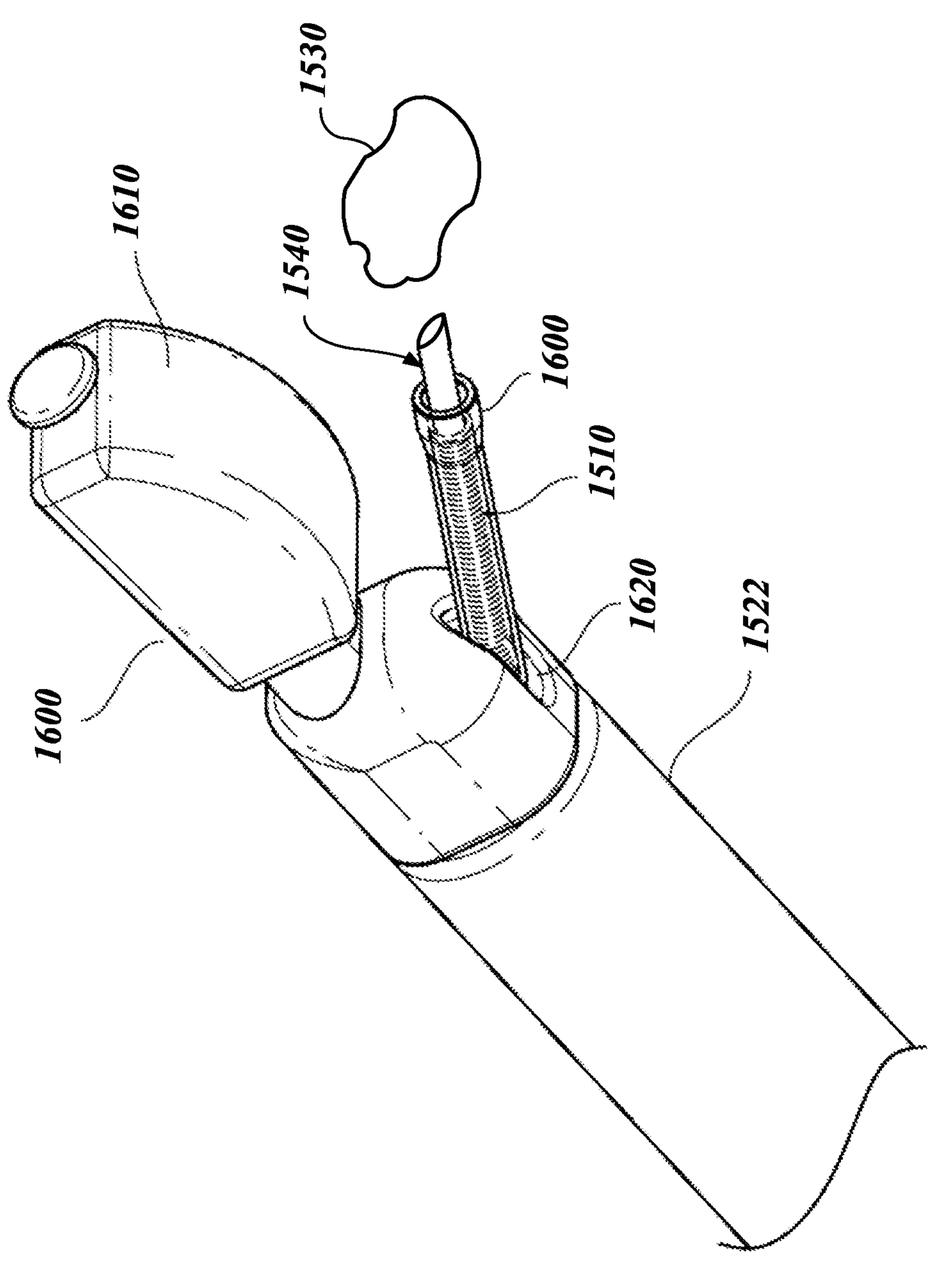
FIG. 16 is perspective view of a head of the insertion system through which the flexible needle may be extended.

Referring additionally to FIG. 16, a head 1600 of the insertion system 1500 (FIG. 15) includes an imaging transducer 1610, such as an ultrasound transducer or a camera. In various embodiments, the head 1600 is disposed at a distal end of the insertion tube 1522. The head 1600 also may include an exit port 1620 through which an elongated instrument, such as the flexible needle 1510, that is conveyed through the insertion tube 1522 may exit the head 1600. In various embodiments, the elongated instrument may be conveyed in a sheath 1630 that extends through the insertion tube 1522. The imaging transducer 1610 collects imaging data that may be presented to an operator, such as via the display 1560 (FIG. 15) to help the operator guide the distal end 1540 of the flexible needle 1510 to the targeted region of tissue 1530 and/or to engage the targeted region of tissue 1530 with the flexible needle 1510 to secure a sample.

With reference to FIGS. 15 and 16, it will be appreciated that the flexible needle 1510 may follow a tortuous path through and beyond the insertion system 1500 to reach a desired target. Having a controlled degree of flexibility at various points along the length of the flexible needle 1510 may be important in enabling the flexible needle to reach the desired location. At the same time, having a degree of column strength and rigidity may be important to be able to press the flexible needle 1510 into a desired location. The use of interrupted cut sections that extend continuously into an uninterrupted cut section enables selected degrees of flexibility while also dispersing stress and strain to avoid undesirable deformation or structural failure of the flexible needle.

Figure 17:
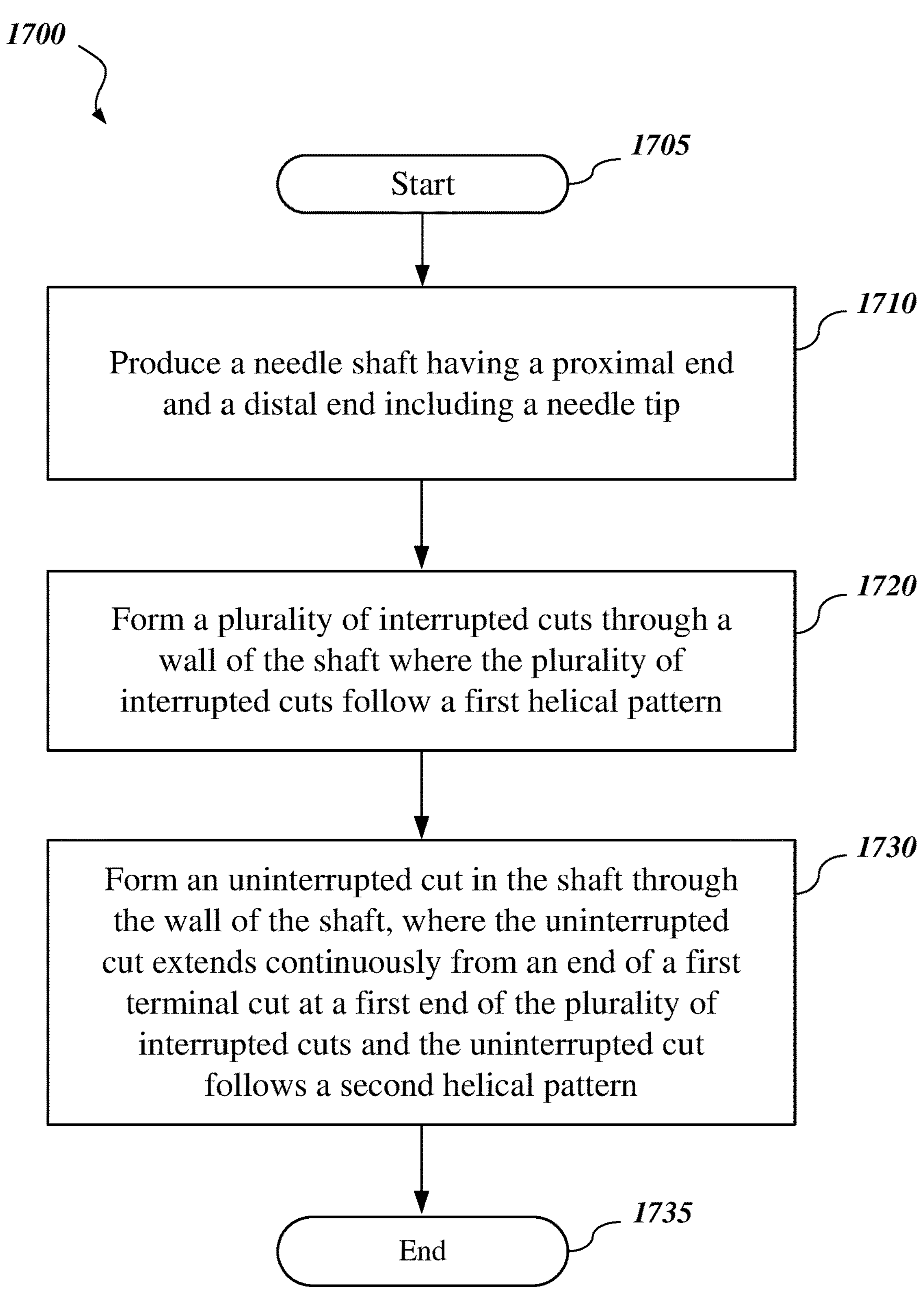
FIG. 17 is a flow chart of an illustrative method of providing a flexible needle.

Referring now to FIG. 17, an illustrative method 1700 of forming a flexible needle is provided. The method 1700 starts at a block 1705. At a block 1710, a needle shaft is produced, where the needle has a proximal end and a distal end including a needle tip. At a block 1720, a plurality of interrupted cuts is formed through a wall of the shaft where the plurality of interrupted cuts follow a first helical pattern. At a block 1730, an uninterrupted cut is formed in the shaft through the wall of the shaft, where the uninterrupted cut extends continuously from an end of a first terminal cut at a first end of the plurality of interrupted cuts and the uninterrupted cut follows a second helical pattern. The method 1700 stops at a block 1735.

Figure 18:
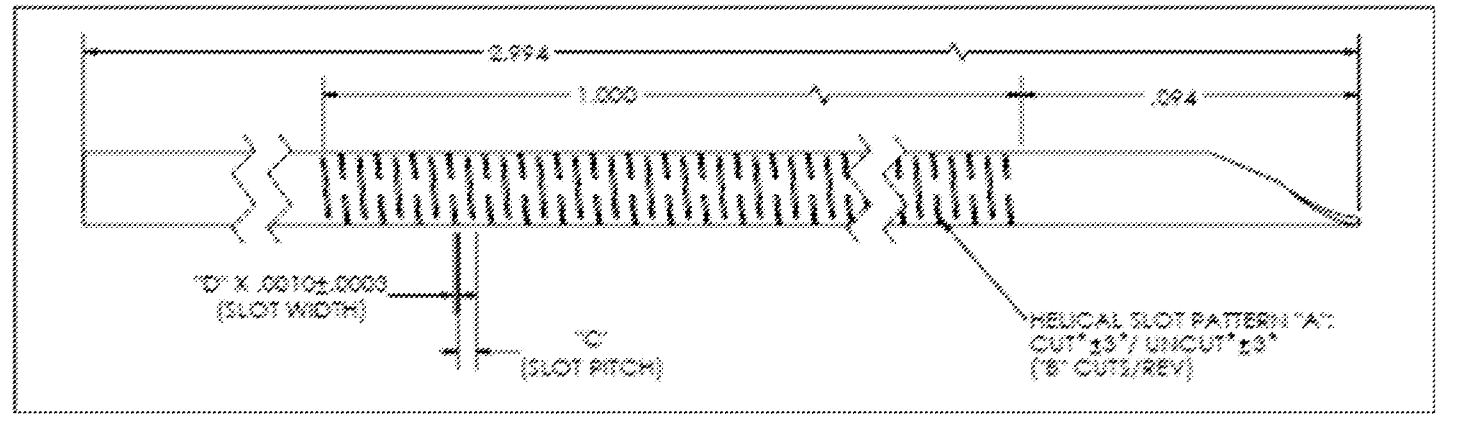
FIG. 18 is a schematic drawing of an exemplary interrupted cut pattern with a table of exemplary numerical values for parameters thereof.

Referring now to FIG. 18, illustrated is a schematic drawing of an exemplary interrupted cut pattern with a table of exemplary numerical values for parameters of exemplary embodiments thereof. In embodiment 1, the interrupted cut pattern includes individual cuts (of a series or sequence of cuts) which traverse radially around a needle along a helical path for 115 degrees (e.g., about 2 radians) before being interrupted by individual uncut sections of 29 degrees (e.g., about 0.5 radians) after which another individual cut begins along the same helical path and traverses for another 115 degrees before being interrupted by yet another uncut section of 29 degrees. This sequence may continue the entire length of the uncut section. As shown in the table of FIG. 18, embodiment 1 includes approximately 2.5 cuts per revolution as a result of the helical slot pattern of 115/29. All numerical values illustrated in FIG. 18 in relation to example embodiments 1-7 are in inches.

It will be appreciated that the present descriptions of the flexible needle apparatuses, systems using the flexible needle apparatus, and methods described herein may be used for any number of applications. Although examples of the system describe securing a sample from a region of targeted tissue, the flexible needle could be used in applications to deposit a substance, sample or drain liquid, or any number of applications.

In some instances, one or more components may be referred to herein as "configured to," "configured by," "configurable to," "operable/operative to," "adapted/adaptable," "able to," "conformable/conformed to," etc. Those skilled in the art will recognize that such terms (for example "configured to") generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (for example, "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (for example, the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

While the disclosed subject matter has been described in terms of illustrative embodiments, it will be understood by those skilled in the art that various modifications can be made thereto without departing from the scope of the claimed subject matter as set forth in the claims.

What is claimed is:

1. An apparatus comprising:

a flexible needle, wherein the flexible needle includes:

a proximal end;

a distal end including a needle tip; and a shaft extending between the proximal end and the distal end and including a flexible portion, wherein the flexible portion includes:

an interrupted cut section including a plurality of interrupted cuts in the shaft following a first helical pattern, an uninterrupted cut section including an uninterrupted cut in the shaft following a second helical pattern, and a continuous transition cut extending continuously from an end of a first terminal cut at a first end of the interrupted cut section into the uninterrupted cut section, wherein the first terminal cut is a final interrupted cut of the plurality of interrupted cuts following the first helical pattern.

2. The apparatus of claim 1, wherein the interrupted cut section is disposed adjacent the distal end and the uninterrupted cut section is disposed between the interrupted cut section and the proximal end.

3. The apparatus of claim 1, wherein the uninterrupted cut section is disposed adjacent the distal end and the interrupted cut section is disposed between the uninterrupted cut section and the proximal end.

4. The apparatus of claim 1, wherein a first pitch angle of the first helical pattern of the interrupted cut section is less than a second pitch angle of the second helical pattern of the uninterrupted cut section.

5. The apparatus of claim 1, wherein a first pitch angle of the first helical pattern of the interrupted cut section includes a pitch angle chosen from a fixed pitch angle and a variable pitch angle.

6. The apparatus of claim 1, wherein a second pitch angle of the second helical pattern of the uninterrupted cut section includes a pitch angle chosen from a fixed pitch angle and a variable pitch angle.

7. The apparatus of claim 1, wherein the plurality of interrupted cuts includes a plurality of linear cuts.

8. The apparatus of claim 1, wherein the plurality of interrupted cuts includes a plurality of nonlinear cuts including at least one cut pattern chosen from a sinusoidal cut pattern, a jigsaw cut pattern, and a zigzag cut pattern.

9. The apparatus of claim 1, wherein at least a portion of the interrupted cuts terminate at a rounded hole formed in the shaft.

10. The apparatus of claim 1, further comprising at least one additional cut section chosen from:

an additional uninterrupted cut section including an additional uninterrupted cut in the shaft following a third helical pattern having a third pitch angle and extending from a second end of a second terminal cut of the plurality of interrupted cuts at an opposite end of the interrupted cut section from the first terminal cut; and an additional interrupted cut section including an additional plurality of interrupted cuts in the shaft following a fourth helical pattern having a fourth pitch angle and extending from an opposing end of the uninterrupted cut from the end of the first terminal cut.

11. A system for sampling a targeted region of tissue, the system comprising:

an insertion system configured to receive an elongated instrument into a proximal end of a lumen and to convey a distal end of the lumen into a body toward a targeted region of tissue to be sampled; and a flexible needle assembly configured to be insertable into the body via the lumen, wherein the flexible needle assembly includes:

a flexible needle, wherein the flexible needle includes:

a proximal end;

a distal end including a needle tip; and a shaft extending between the proximal end and the distal end and including a flexible portion, wherein the flexible portion includes:

an interrupted cut section including a plurality of interrupted cuts in the shaft following a first helical pattern;

an uninterrupted cut section including an uninterrupted cut in the shaft following a second helical pattern; and a continuous transition cut extending between the interrupted cut section and the uninterrupted cut section, wherein the continuous transition cut extends continuously from an end of a first terminal cut at a first end of the interrupted cut section into the uninterrupted cut section, wherein the first terminal cut is a final interrupted cut of the plurality of interrupted cuts following the first helical pattern; and a handle assembly configured to engage the proximal end of the flexible needle and to control movement of the flexible needle.

12. The system of claim 11, wherein the interrupted cut section is disposed adjacent the distal end and the uninterrupted cut section is disposed between the interrupted cut section and the proximal end.

13. The system of claim 11, wherein the uninterrupted cut section is disposed adjacent the distal end and the interrupted cut section is disposed between the uninterrupted cut section and the proximal end.

14. The system of claim 11, wherein a first pitch angle of the first helical pattern of the interrupted cut section is less than a second pitch angle of the second helical pattern of the uninterrupted cut section.

15. The system of claim 11, wherein a first pitch angle of the first helical pattern of the interrupted cut section includes a pitch angle chosen from a fixed pitch angle and a variable pitch angle.

16. The system of claim 11, wherein a second pitch angle of the second helical pattern of the uninterrupted cut section includes a pitch angle chosen from a fixed pitch angle and a variable pitch angle.

17. The system of claim 11, wherein the plurality of interrupted cuts includes a plurality of linear cuts.

18. The system of claim 11, wherein the plurality of interrupted cuts includes a plurality of nonlinear cuts including at least one cut pattern chosen from a sinusoidal cut pattern, a jigsaw cut pattern, and a zigzag cut pattern.

19. The system of claim 11, wherein at least a portion of the interrupted cuts terminate at a rounded hole formed in the shaft.

20. The system of claim 11, further comprising at least one additional cut section chosen from:

an additional uninterrupted cut section including an additional uninterrupted cut in the shaft following a third helical pattern having a third pitch angle and extending from a second end of a second terminal cut of the plurality of interrupted cuts at an opposite end of the interrupted cut section from the first terminal cut; and an additional interrupted cut section including an additional plurality of interrupted cuts in the shaft following a fourth helical pattern having a fourth pitch angle and extending from an opposing end of the uninterrupted cut from the end of the first terminal cut.

21. The system of claim 11, wherein the insertion system further includes an imaging probe deployable at the distal end of the lumen to monitor a position of the needle relative to the targeted region of tissue to be sampled.

* * * * *